United States Patent
Bell et al.

(10) Patent No.: US 8,211,829 B2
(45) Date of Patent: Jul. 3, 2012

(54) AGROCHEMICAL CONCENTRATE COMPRISING AN ADJUVANT AND A HYDROTROPE

(75) Inventors: Gordon Bell, Bracknell (GB); Guy Ramsay, Bracknell (GB)

(73) Assignee: Syngenta Crop Protection LLC, Greensboro, NC (US)

( * ) Notice: Subject to any disclaimer, the term of this patent is extended or adjusted under 35 U.S.C. 154(b) by 368 days.

(21) Appl. No.: 10/567,230

(22) PCT Filed: Aug. 6, 2004

(86) PCT No.: PCT/GB2004/003424
§ 371 (c)(1),
(2), (4) Date: Feb. 3, 2006

(87) PCT Pub. No.: WO2005/013692
PCT Pub. Date: Feb. 17, 2005

(65) Prior Publication Data
US 2006/0252648 A1    Nov. 9, 2006

(30) Foreign Application Priority Data
Aug. 6, 2003 (GB) .................................. 0318448.8

(51) Int. Cl.
*A01N 25/00* (2006.01)
(52) U.S. Cl. .................................................. 504/116.1
(58) Field of Classification Search ................ 504/116.1
See application file for complete search history.

(56) References Cited

U.S. PATENT DOCUMENTS 5,708,073 A * 1/1998 Dodge et al. .................. 524/590

FOREIGN PATENT DOCUMENTS

| EP | 0074329 A | | 3/1983 |
|---|---|---|---|
| EP | 1023832 | * | 8/2000 |
| GB | 1453443 A | | 10/1976 |
| GB | 1483186 A | | 8/1977 |
| WO | WO 94/05751 A | | 3/1994 |
| WO | WO 98/32821 A | | 7/1998 |
| WO | WO 98/37760 A | | 9/1998 |
| WO | WO 01/17351 | | 3/2001 |

OTHER PUBLICATIONS

Hill et al., eds., Alkyl Polyglycosides: Technology, Properties and Application, 1997, pp. 14-18, 20 and 39-40 (VCH Verkagsgesellschaft mbh, D-69451 Weinheim DE).*
Karlheinz Hill et al., eds. Alkyl Polyglycosides: Technology Properties and Applications, pp. 14-18, 20 and 39-40 (VCH Verlagsgesellschaft mbh, D-69451 Weinheim DE), 1997.

* cited by examiner

*Primary Examiner* — Alton Pryor
(74) *Attorney, Agent, or Firm* — William A. Teoli, Jr.

(57) ABSTRACT

Agrochemical concentrates having a continuous water-containing single phase, where said continuous phase also comprises an oil-based adjuvant and a hydrotrope capable of solubilizing said adjuvant in said continuous phase, a process for making these concentrates and a method of using these concentrates.

20 Claims, No Drawings

AGROCHEMICAL CONCENTRATE COMPRISING AN ADJUVANT AND A HYDROTROPE

This application is a 371 of International Application No. PCT/GB2004/003424 filed Aug. 6, 2004, which claims priority to GB 0318448.8 filed Aug. 6, 2003, the contents of which are incorporated herein by reference.

This invention relates to a formulation and in particular to an aqueous-based formulation concentrate, for example an aqueous-based agrochemical formulation concentrate, to a process for making these formulations and to a method of using these formulations.

Agrochemical formulation concentrates are often sold as aqueous-based compositions. A formulation concentrate is intended to be diluted prior to application, for example by spraying. Aqueous-based formulation concentrates are desirable since they may avoid or reduce the need for solvents [used in formulation types such as emulsifiable concentrates, ECs], have good handling characteristics, are not flammable, generally have low toxicity, low phyto-toxicity, have inexpensive raw materials, low manufacturing costs and have a low odour.

It is known that aqueous-based compositions can be chosen from a number of formulation types, including soluble concentrates (SL), emulsions (both oil in water (EW) and water in oil (EO)), micro-emulsions (ME), suspension concentrates (SC) and capsule suspensions (CS). The formulation type chosen in any instance depends upon the particular purpose envisaged and the physical, chemical and biological properties of the components of the composition.

Soluble Concentrates (SL) may be prepared by dissolving a compound, for example an agrochemical, in water. These solutions may contain a surface active agent (for example to improve water dilution or prevent crystallisation in a spray tank).

Oil-in-water emulsions (EW) may be prepared by dissolving a compound, for example an agrochemical, in an organic solvent (optionally containing one or more wetting agents, one or more emulsifying agents or a mixture of said agents). Preparation of an agrochemical EW may involve obtaining an agrochemical either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more surface active agents [SFAs], under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water. Water-in-oil emulsions (EO) may be prepared in a similar way to EWs and if a very high oil loading is required or if the nature of the components dictate then they may be more suitable than an EW; the EO formulation is two-phase and is designed to phase-invert upon addition to a spray-tank of water.

SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting).

Microemulsions (ME) may be prepared by mixing water with a blend of one or more solvents with one or more SFAs, to produce spontaneously a thermodynamically stable liquid formulation. To prepare an agrochemical ME, an agrochemical is present initially in either the water or the solvent/SFA blend. Suitable solvents for use in MEs include those hereinbefore described for use in EWs. An ME may be either an oil-in-water or a water-in-oil system (which system is present may be determined by conductivity measurements) and may be suitable for mixing water-soluble and oil-soluble agrochemicals in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles. Agrochemical SCs may be prepared by ball or bead milling a solid agrochemical in a suitable medium, optionally with one or more dispersing agents, to produce a fine particle suspension of the agrochemical. One or more wetting agents may be included in the composition and a suspending agent may be included to reduce the rate at which the particles settle. Alternatively, an agrochemical may be dry milled and added to water, containing agents hereinbefore described, to produce the desired end product.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains an agrochemical and, optionally, a carrier or diluent therefor. The polymeric shell may be produced by either an interfacial polycondensation reaction or by a coacervation procedure. Agrochemical compositions may provide controlled release of an agrochemical, reduce operator exposure to an agrochemical or they may be used for seed treatment.

Some compositions may contain a mixture of an agrochemical with one or more other agrochemicals or other additives. Some mixtures may comprise agrochemicals or additives that have significantly different physical, chemical or biological properties such that they do not easily lend themselves to the same conventional formulation type. In these circumstances other formulation types may be prepared. For example, where one agrochemical is a water insoluble solid and another agrochemical is a water insoluble liquid, it may nevertheless be possible to disperse each agrochemical in the same continuous aqueous phase by dispersing the solid agrochemical as a suspension (using a preparation analogous to that of an SC) but dispersing the liquid agrochemical as an emulsion (using a preparation analogous to that of an EW). The resultant composition is a suspoemulsion (SE) formulation.

The term "agrochemicals" includes herbicides, fungicides and insecticides.

Dispersing aids are generally used to maintain solids or liquids in dispersion and adjuvants are commonly used to enhance the bioperformance (activity) of an agrochemical. Adjuvants can vary in complexity from simple surfactants to multi-component blends of oils. Such adjuvants may be "tank-mix" adjuvant systems which are added to agricultural spray tanks separately from an agrochemical formulation but it is more convenient to provide a formulation where all necessary dispersing aids and adjuvants are incorporated directly in ("built-in") to a formulation concentrate, such as an SC, EW, SE, SL, CS or ME. This ensures that the farmer will use the correct adjuvant, and also controls the ratio of adjuvant to agrochemical. Oil-based adjuvants are particularly useful in enhancing the bioperformance of an agrochemical but are also inherently difficult to build-in to an aqueous concentrate at a desirably high concentration. As used herein, the term "oil-based adjuvant" means a liquid adjuvant or mixture of adjuvants that is substantially insoluble in the aqueous continuous phase of the agrochemical concentrate.

SC, EW, SE, SL, CS or ME formulation concentrates may be formulated with surfactants and oil blends but this often leads to problems of incompatibility, particularly since the concentrates are required to be physically stable over extended periods of time and under the extremes of temperature encountered during commercial use. Stability problems may include flocculation, heteroflocculation, crystal growth of a dispersed solid, creaming of a dispersed liquid, creaming of an adjuvant/surfactant system, phase separation and chemical decomposition.

Canadian Patent 1186217 discloses the use of a hydrotrope to solubilise a liquid agrochemical in to water, optionally in the presence of a small concentration of a functional aid.

It is desirable therefore to provide a physically stable agrochemical concentrate whether it is a "tank-mix" or a "built-in" formulation containing a bioperformance enhancing oil-based adjuvant at high loading. The present invention meets this need through the use of hydrotropes.

In the context of the present invention an agrochemical concentrate does not necessarily contain an agrochemical compound; the agrochemical concentrate may simply be an adjuvant system intended for "tank-mixing" with another agrochemical concentrate which does contain an agrochemical compound.

According to the present invention there is provided an agrochemical concentrate having a continuous water-containing single phase which is characterised in that said continuous phase also comprises an oil-based adjuvant and a hydrotrope capable of solubilising said adjuvant in the continuous phase.

In another aspect, the present invention provides an aqueous agrochemical suspension concentrate comprising an oil-based adjuvant and a hydrotrope capable of solubilising said adjuvant in the aqueous phase.

A hydrotrope is a substance that, at high concentrations, enhances the solubility of non-polar compounds (oils) in water. In the literature, there are some inconsistent discussions of the properties of hydrotropes; for the purpose of the present invention, hydrotropes are considered to be substances which are highly water soluble and amphiphilic and which do not form micelles when present alone in water at concentrations below 50% by weight. Solubilisation of oils by hydrotropes is characterised by the relatively high concentrations of the hydrotropes needed and the larger amount of oil solubilised compared with that observed for conventional micellar surfactants. Examples of hydrotropes which may be used in the present invention include anionic benzoates, anionic benzosulphonates, anionic phosphates and phosphonates, anionic benzophosphates, alkylarylphosphates and phosphonates, neutral phenols such as catechol and resorcinol, aliphatic glycolsulfates, alicyclic bile salts, aliphatic carboxylates, aromatic carboxylates, naphthalene sulphonates, alkynaphthalene sulphonates, polymeric naphthalene sulphonates and their copolymers, alkyl aryl sulphonates and carboxylates and their polymers and copolymers, naphthalene and alkylnaphthalene phosphates and phosphonates and their polymers and copolymers, glycol and glycerol ethers and the amino acid proline. In general a given hydrotrope will solubilise a specific group of oils or oil blends. Simple test tube experiments enable a potential hydrotrope/oil mixture to be assessed quickly and easily; hydrotropic mixtures form a single phase which can be detected by eye.

As examples of oil-based agrochemical adjuvants suitable for use in combination with the above hydrotropes there may be mentioned seed oils, methylated seed oils, triglycerides of fatty acids and fatty amines, methyl esters of fatty acids and fatty amines, mineral oils which can be linear, branched or mixtures of linear and branched, aromatic oils, fatty alcohols, fatty acids, fatty amines, aliphatic alcohols, aliphatic amines, aliphatic esters, aliphatic carboxylic acids, aliphatic ketones, aliphatic aldehydes, aliphatic amides, aromatic carboxylic acids, aromatic alcohols and phenols, aromatic ketones, aromatic aldehydes, aromatic amines or anilines or anilides, aromatic amides, natural products such as terpenes, sesquiterpenes and diterpenes, alkyl or aryl or alkylaryl phosphates and phosphonates. Included also are halogenated variants of the forementioned oils. Similarly ethoxylated variants of the alcohols, amines and acids mentioned are also suitable providing the degree of ethoxylation is not too long, for example having an average degree of ethoxylation below 4. BRIJ 92, oleyl alcohol ethoxylate with an average of 2 moles of ethoxylate is an example of a suitable ethoxylated fatty alcohol and ETHOMEEN S12 is an example of a short chain ethoxylated fatty amine. Silicone oils are also suitable. Oil blends may also be used, for example TURBOCHARGE (Syngenta Limited), which is a proprietary blend of oils and short chain ethoxylates. Other commercially available blends of oils and short chain ethoxylates include MERGE, DASH, BREAK-THRU 464 and AGRIDEX products. The commercial product AGRAL 90 is a blend of ethoxylated nonylphenols.

Another group of oil adjuvants includes the long chain ethoxylate versions of synthetic or fatty acids, alcohols and amines. These adjuvants are unusual in that they from viscous, hexagonal or cubic phases at high concentrations in water. Hydrotropes may be used to prevent this from happening, thus allowing high loadings to be achieved in agrochemical concentrates of the present invention. As examples of preferred combinations of hydrotrope and oil-based adjuvants suitable for use to improve the bioperformance of agrochemicals, there may be mentioned:

(a) Benzosulphonate hydrotropes such as ammonium cumene sulphonate and ammonium xylene sulphonate in combination with fatty alcohols, fatty acids or fatty amines and simple derivatives thereof such as methyl esters and adjuvant oils derived from plant terpenes.

(b) Anionic alkylaryl carboxylatehydrotropes such as the potassium salt of 5(6)-carboxy-4-hexyl-2-cyclohexene-1 octanoic acid (commercially available under the trade name WESTVACCO H240) in combination with fatty alcohols, fatty acids or fatty amines and simple derivatives thereof such as methyl esters and short chain ethoxylates, especially when these materials are also blended with linear or branched mineral oils.

(c) Phenol type hydrotropes, such as sodium salicylate, in combination with long chain ethoxylate versions of synthetic or fatty acids, alcohols and amines.

As preferred examples of combinations of type (a) above there may be mentioned the hydrotrope ammonium cumene sulphonate in combination with oleyl alcohol or the plant terpene phytol or the plant terpene geraniol and the hydrotrope ammonium xylene sulphonate in combination with the plant terpene geraniol. As preferred combinations of type (b) above there may be mentioned the hydrotrope 5(6)-carboxy-4-hexyl-2-cyclohexene-1 octanoic acid in combination with oleyl alcohol or the commercially available adjuvant TURBOCHARGE. As preferred combinations of type (c) above there may be mentioned the hydrotrope sodium salicylate in combination with ETHOMEEN T25 [a tallow amine ethoxylate]. We have found that for agrochemicals such as selective herbicides, insecticides and fungicides that are not intended to harm the target plant, the built-in combination of the oil-based adjuvant and the hydrotrope may often be less phytotoxic to target plants than the conventional tank-mixed adjuvant system, whilst delivering equivalent biological activity. The hydrotrope system also offers biological advantages in that the agrochemical concentrates of the present invention may also deliver equivalent biological activity to conventional formulation concentrates despite using smaller amounts of the oil-based adjuvant.

Therefore, in another aspect of the invention, there is provided the use of an agrochemical concentrate of this invention to provide low phytotoxicity.

It is to be understood that the hydrotrope solubilises the oil-based adjuvant into the aqueous medium in which an agrochemical is optionally dispersed in the concentrate of the present invention. The aqueous medium need not necessarily be a true solution in the physical sense but will appear to be a single phase to the eye and under the microscope and will remain as such over extended storage periods, and in many instances essentially indefinitely. It is a further advantage of the hydrotrope solubilised systems of the present invention, not only that relatively high levels of oil-based adjuvant may be incorporated but also that the resultant composition has a relatively low viscosity. Such compositions are poured from a container without difficulty and without leaving excessive residues in the container. The composition is readily diluted in the spray tank and any residues remaining in an empty container are simply and easily rinsed out. The compositions of the invention are typically Newtonian fluids with viscosity less than 1000 cP at room temperature.

The present invention does not depend critically on the nature of the agrochemical present in the formulation concentrate. Those skilled in the art will be well aware of the criteria for a given agrochemical to be suitable for a specific formulation type. As examples of herbicides suitable for formulation as a concentrate there may be mentioned mesotrione, fomesafen, tralkoxydim, napropamide, amitraz, propanil, pyrimethanil, dicloran, tecnazene, toclofos methyl, flamprop M, 2,4-D, MCPA, mecoprop, clodinafop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bifenox, oxyfluorfen, acifluorfen, fluoroglycofen-ethyl, bromoxynil, ioxynil, imazamethabenzmethyl, imazapyr, imazaquin, imazethapyr, imazapic, imazamox, flumioxazin, flumiclorac-pentyl, picloram, amnodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron and metoxuron.

As examples of fungicides suitable for formulation as a concentrate there may be mentioned azoxystrobin, trifloxystrobin, kresoxim methyl, famoxadone, metominostrobin and picoxystrobin, cyprodanil, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, triticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin and prothioconazole.

As examples of insecticides suitable for formulation as a concentrate there may be mentioned thiamethoxam, imidacloprid, acetamiprid, clothianidin, dinotefuran, nitenpyram, fipronil, abamectin, emamectin, bendiocarb, carbaryl, fenoxycarb, isoprocarb, pirimicarb, propoxur, xylylcarb, asulam, chlorprophamn, endosulfan, heptachlor, tebufenozide, bensultap, diethofencarb, pirimiphos methyl, aldicarb, methomyl, cyprmethrin, bioallethrin, deltamethrin, lambda cyhalothrin, cyhalothrin, cyfluthrin, fenvalerate, imiprothrin, permethrin, halfenprox and tefluthrin.

The foregoing lists are not intended to be exhaustive and other examples will occur to those skilled in the art.

The agrochemical concentrate of the present invention may also incorporate one or more surfactants or dispersing agents to assist the dispersion of an agrochemical in the aqueous medium (dispersant system). The dispersant system will not generally contribute to enhancement of the bioperformance of the agrochemical and is present primarily to assist in maintaining the dispersed agrochemical in dispersion. Conversely the oil-based adjuvant will not generally assist directly in maintaining the agrochemical in dispersion. Many individual dispersants and mixtures thereof suitable for forming a dispersant system for a concentrate are known to those skilled in the art and a very wide range of choices is available. Typical dispersants that may be used to form a dispersant system include copolymers of ethylene oxide and propylene oxide, aryl and alkyl aryl sulphonate copolymers with formaldehyde such as naphthalene sulphonate formaldehyde copolymers, salts of the copolymers of acrylic acid with diisobutylene or ethylene oxide or styrene or vinyl pyrrolidone, salts of copolymers of styrene sulphate with ethylene oxide or diisobutylene or vinyl pyrrolidone or propylene oxide, tristyrylphenol type dispersants where the phenol has been ethoxylated and optionally sulphonated or phosphated, alkylphenol ethoxylates, polyvinyl alcohol and substituted or sulphated polyvinyl alcohols, polyvinyl pyrrolidone and its copolymers.

The agrochemical is conventionally present in the concentrate at a concentration between 5 and 60% and typically of about 10 to 35% by weight. The hydrotrope is suitably present in the concentrate at a concentration of from 5 to 50% and typically from about 15 to 30% by weight. The oil-based adjuvant is suitably present at a concentration of greater than or equal to 10%, conveniently from 10 to 60% and typically from 10 to 40% by weight. The dispersant system is typically present at a concentration of total dispersant of from 0 to 40% and preferably from 0 to 20% by weight. The dispersant system may comprise a mixture of dispersants. A typical example of a mixture of dispersants includes a copolymer of ethylene oxide and propylene oxide, such as Atlox 4894 or Atlox 4896 [ATLOX is a trademark], in a quantity from 0 to 20% for example from 1 to 8% w/w combined with a further dispersant such as Atlox 10/5 or Brij 96 in a concentration of 0 to 20%, for example from 1 to 9% w/w.

The ratio of oil-based adjuvant to hydrotrope suitably varies from 1:10 to 10:1, for example from 1:3 to 3:1.

In a further aspect, the present invention provides an agrochemical concentrate as described above which contains a second phase dispersed in the continuous single phase. In one aspect, the second phase is a solid [this aspect includes SC formulations of the invention]. In another aspect, the second phase comprises a water-immiscible liquid [this aspect includes EW formulations of the invention]. Conveniently, the second phase is micro-encapsulated [this aspect includes CS formulations of the invention]. Alternatively, the second phase may be a micro-emulsion [this aspect includes ME formulations of the invention].

In a still further aspect, the present invention provides an agrochemical concentrate as described above which contains a third phase comprising a water-immiscible liquid dispersed in the continuous single phase [this aspect includes SE formulations of the invention].

In yet another aspect, the present invention provides an agrochemical concentrate comprising an agrochemical dissolved in the continuous phase.

In another aspect, the present invention provides an agrochemical concentrate where the second phase comprises an agrochemical.

In yet another aspect, the present invention provides an agrochemical concentrate as described above where the second phase comprises an agrochemical or the third phase comprises an agrochemical or both these phases each comprise an agrochemical which may be the same or different agrochemicals.

In an additional aspect, the present invention provides which a continuous oil phase in which is dispersed an agrochemical concentrate as described above [this aspect includes EO formulations of the invention].

The formulation concentrates of the present invention may be prepared by conventional techniques. However, previously, conventional techniques have not permitted an oil-based adjuvant readily to be introduced early in the process, mainly due to viscosity-related problems. Since the use of a hydrotrope with the oil-based adjuvant reduces these viscosity problems it has now been found that it is possible to prepare the continuous phase of the present invention first and then for any subsequent processing to take place in that said continuous phase. This enables preparation of high concentration products, faster production, use of fewer production vessels and leads to overall process cost reduction.

Therefore, according to another aspect of the present invention there is provided a process for the manufacture of an agrochemical concentrate of the present invention where the continuous phase is prepared first and then any subsequent processing takes place in that said continuous phase.

A suspension concentrate may be made using conventional techniques. Typically in commercial practice, a solid herbicide is milled in water until the desired particle size is reached. The particle size is typically from 0.5 to 15 microns, for example from 1 to 5 microns volume median diameter. A dispersant system is generally added before milling so that it is present during the milling process. The stage at which the hydrotrope and oil-based adjuvant are added is not critical. It is generally convenient to add the hydrotrope together with the oil to the aqueous system before, during or after milling.

According to another aspect of the present invention there is provided a process for the manufacture of a suspension concentrate which comprises milling a solid agrochemical in water, optionally in the presence of a dispersant system, characterised in that there is incorporated in the composition a hydrotrope and an oil-based adjuvant for the agrochemical.

The invention is illustrated by the following non-limiting. Examples in which all parts and percentages are by weight unless otherwise stated. Whilst the majority of the Examples relate to an aqueous agrochemical suspension concentrate, they could be modified readily to other formulation types.

The composition of the products used in the Examples was as follows:—

Morwet D425—A commercially available anionic naphthalene sulphonate formaldehyde condensate copolymer, sold by Crompton Corporation Synperonic 10/5—A commercially available surfactant comprising a short chain branched alcohol with five moles of ethylene oxide. Sold by Uniqema Ltd.

Atlox 4896—A copolymer condensate of ethylene and propylene oxide, sold by Uniqema Ltd.

Atlox 4913—A copolymer condensate of ethylene oxide with methyl methacrylate, sold by Uniqema Ltd.

Atlox 4894—A copolymer condensate of ethylene and propylene oxide, sold by Uniqema Ltd.

Brij 96—A fatty alcohol condensed with an average of 10 moles of ethylene oxide. Sold by Uniqema Ltd.

Eltesol AC 60—Ammonium cumene sulphonate supplied by Albright and Wilson Ltd.

EXAMPLE 1

The herbicide tralkoxydim (10%) having a particle size of about 50 microns, Morwet D425 (8%), Westvacco H240 (29%), Turbocharge (30%), Synperonic 10/5 (6%) and water (17%) to a total weight of 5 g was added to a glass vial. The Westvacco H240 was the hydrotrope and the Turbocharge was the oil-based adjuvant. Morwet D425 and Synperonic 10/5 together formed the dispersant system. The mixture was gently swirled and sheared for one minute using an Ystral mixer, which reduced the particle size of the tralkoxydim to a volume mean of 25 microns. An equal volume of No 4 zirconia beads was added to the vial which was then shaken for 30 minutes in a laboratory shaker.

The sample could be both poured and pipetted easily and this was taken as an indication that the viscosity was satisfactory (viscosity test). The sample dispersed readily in water without agitation, at a dilution of 1% and a standing time of one minute (dilution test).

The sample also passed a standard flocculation test. In this test a 1% dilution of the sample was made using CIPAC standard hard water C. The sample was inverted to ensure homogeneity and was left to stand for one hour. After this time it was examined by microscope to observe any signs of flocculation. If there were no signs of flocculation the sample met the flocculation test.

EXAMPLES 2 TO 5

The procedure described in example 1 was repeated for the samples shown in Table 1. These samples all contained the commercial herbicide tralkoxydim with the commercial tank mix adjuvant Turbocharge. All samples passed the viscosity, dilution and flocculation tests.

TABLE 1

| | Composition in % by weight | | | | | |
|---|---|---|---|---|---|---|
| Example No | Tralkoxydim | Morwet D425 | Westvacco H240 | Turbocharge | Synperonic 10/5 | Water |
| 2 | 12 | 4 | 25 | 38 | 0 | 21 |
| 3 | 16 | 5 | 27 | 25 | 0 | 27 |
| 4 | 15 | 5 | 25 | 25 | 5 | 25 |
| 5 | 16 | 2 | 25 | 22 | 0 | 35 |

EXAMPLES 6 TO 11

The compositions listed in Table 2 were prepared using the procedure of Example 1. In each case however the dispersant Morwet D425 has been replaced with Atlox 4894. All samples passed the viscosity, dilution and flocculation tests.

TABLE 2

| Example No | Tralkoxydim | Westvacco H240 | Turbocharge | Synperonic 10/5 | Atlox 4894 | Water |
|---|---|---|---|---|---|---|
| 6 | 10 | 25 | 17 | 9 | 8 | 31 |
| 7 | 10 | 30 | 25 | 8 | 6 | 21 |
| 8 | 10 | 20 | 30 | 3 | 8 | 29 |
| 9 | 13 | 19 | 26 | 3 | 8 | 31 |
| 10 | 10 | 22 | 11 | 5 | 0 | 52 |
| 11 | 20 | 31 | 20 | 7 | 8 | 14 |

Composition in % by weight

EXAMPLES 12 TO 15

The compositions listed in Table 3 were prepared using the procedure of Example 1. The Examples illustrate the use of different dispersant systems. All samples passed the viscosity, dilution and flocculation tests. In Table 3, D1 is Atlox 4896, D2 is Atlox 4913, D3 is Atlox 4894 and D4 is Morwet D425

TABLE 3

| Example No | Tralkoxydim | Westvacco H240 | Turbocharge | Synperonic 10/5 | Water | D1 | D2 | D3 | D4 |
|---|---|---|---|---|---|---|---|---|---|
| 12 | 20 | 31 | 20 | 7 | 14 | 8 | 0 | 0 | 0 |
| 13 | 20 | 31 | 20 | 7 | 14 | 4 | 4 | 0 | 0 |
| 14 | 20 | 31 | 20 | 7 | 14 | 0 | 0 | 4 | 4 |
| 15 | 20 | 31 | 20 | 7 | 14 | 0 | 0 | 8 | 0 |

Composition in % by weight

EXAMPLES 16 AND 17

The compositions listed in Table 4 were prepared using the procedure of Example 1. The Examples illustrate the use of different dispersant systems. All samples passed the viscosity, dilution and flocculation tests. In Table 4, C1 is Synperonic 10/5, C2 is Brij 96.

TABLE 4

| Example No | Tralkoxydim | Morwet D425 | Westvacco H240 | Turbocharge | Water | C1 | C2 |
|---|---|---|---|---|---|---|---|
| 16 | 15 | 5 | 25 | 25 | 25 | 0 | 5 |
| 17 | 15 | 5 | 25 | 25 | 25 | 5 | 0 |

Composition in % by weight

EXAMPLES 18 AND 19

The compositions listed in Table 5 were prepared using the procedure of Example 1 but used the commercial herbicide diuron in place of tralkoxydim. All samples passed the viscosity, dilution and flocculation tests.

TABLE 5

| Example No | Diuron | Atlox 4894 | Westvacco H240 | Turbocharge | Synperonic 10/5 | Water |
|---|---|---|---|---|---|---|
| 18 | 13 | 8 | 19 | 26 | 3 | 31 |
| 19 | 10 | 8 | 20 | 30 | 3 | 29 |

Composition in % by weight

EXAMPLES 20 TO 23

The compositions listed in Table 6 were prepared using the procedure of Example 1 but used the commercial fungicide picoxystrobin in place of tralkoxydim. All samples passed the viscosity, dilution and flocculation tests.

TABLE 6

| Example No | Picoxystrobin | Atlox 4894 | Westvacco H240 | Turbocharge | Synperonic 10/5 | Water |
|---|---|---|---|---|---|---|
| 20 | 21 | 6 | 27 | 19 | 4 | 23 |
| 21 | 24 | 5 | 27 | 17 | 3 | 24 |
| 22 | 19 | 8 | 26 | 17 | 3 | 27 |
| 23 | 30 | 8 | 31 | 17 | 3 | 11 |

Composition in % by weight

EXAMPLE 24

This example illustrates the formation of a hydrotrope formulation containing the oil oleyl alcohol with the hydrotrope ammonium cumene sulphonate.

Tralkoxydim (10%), Atlox 4894 (8%), Eltesol AC 60 (13%), Oleyl alcohol (30%), Synperonic 10/5 (3%) and water (36%) to a total weight of 5 g was added to a glass vial. The mixture was gently swirled and sheared for one minute using an Ystral mixer. An equal volume of no 4 zirconia beads was added to the vial which was then shaken for 30 minutes in a laboratory shaker. The resulting sample passed the viscosity, dilution and flocculation tests.

EXAMPLE 25

Three hydrotrope formulations were prepared using the method outlined in Example 1. Table 7 shows the ingredients that were used.

TABLE 7

| Composition | Tralkoxydim | Westvacco H240 | Atlox 4894 | Turbocharge | Synperonic 10/5 | Water |
|---|---|---|---|---|---|---|
| H 1 | 20 | 31 | 8 | 20 | 7 | 14 |
| H 2 | 13 | 19 | 8 | 26 | 3 | 31 |
| H 3 | 10 | 20 | 8 | 30 | 3 | 29 |

Composition in % by weight

These samples passed the viscosity, dilution and flocculation tests, and were used for biological testing.

A sample of a commercial tralkoxydim suspension concentrate available under the tradename 'Achieve 25 SC' was used as a reference material. The strength of the suspension concentrate was 25% w/w. The reference material was tank mixed with commercial Turbocharge at two rates, these being 0.2% and 0.5% v/v of the spray tank volume. The ratio by weight of Turbocharge to tralkoxydim in the compositions is given below in Table 11 at an application rate of 50 g/ha. Plant species (weeds against which tralkoxydim is effective) were grown and tested under glasshouse conditions. *Alopecuius myosuroides* (ALOMI), *Avena fatua* (AVEFA), *Echinochloa crus-galli* (ECHCG) and *Lolium rigidum* (LOLRI) were grown to the 2.3 leaf stage and *Setaria viridis* (SETVI) to stage 3.3, and were sprayed with 100 liters/hectare of spray solution using a laboratory track sprayer. The agrochemical application rate was 50 g/ha. Tralkoxydim is a selective herbicide for use on wheat and barley and phytotoxicity against these species is therefore undesirable. The wheat species *Triticum aestivum* (TRZAS) cultivar 'Barrie', and the barley variant *Hordeum vulgaris* (HORVUT) 'Bonanza' were sprayed at rates of 50, 100, 200 and 400 g/ha. The percentage crop damage was assessed at 11 and 22 days after application, and the weed control at 22 days after application.

Table 8 shows the phytotoxicity of each formulation scored as percentage leaf damage on two crop species 11 days after treatment. The score represents the mean value taken from all of the rates, with three replicated of each rate.

TABLE 8

Leaf Damage 11 DAT %

| Composition | TRZAS 'Barrie' | HORVU 'Bonanza' |
| --- | --- | --- |
| H1 | 5 | 2 |
| H2 | 3 | 4 |
| H3 | 10 | 2 |
| Achieve SC' + 0.2% Turbocharge | 13 | 7 |
| Achieve SC' + 0.5% Turbocharge | 15 | 12 |

Table 9 shows the percentage kill for each formulation on five weed species. The top rate of tralkoxydim (50 g/ha) was used and results are the mean of three replicates. At this application rate the ratio of Turbocharge to tralkoxydim for the five formulations is shown in Table 10.

TABLE 9

% Kill against Weed Species

| Formulation | ALOMY | AVEFA | LOLRI | SETVI |
| --- | --- | --- | --- | --- |
| H 1 | 75.0 | 80.0 | 63.3 | 61.7 |
| H 2 | 88.3 | 85.0 | 43.3 | 46.7 |
| H 3 | 86.7 | 93.3 | 68.3 | 73.3 |
| Achieve SC' + 0.2% Turbocharge | 86.7 | 86.7 | 68.3 | 65.0 |
| Achieve SC' + 0.5% Turbocharge | 86.7 | 90.0 | 83.3 | 66.7 |

TABLE 10

Ratio of Turbocharge to Tralkoxydim

| Formulation | Ratio Turbocharge/Tralkoxydim |
| --- | --- |
| H1 | 1 |
| H2 | 2 |
| H3 | 3 |
| Achieve SC' + 0.2% Turbocharge | 3.5 |
| Achieve SC' + 0.5% Turbocharge | 8.75 |

The biological efficacy of each formulation as a weed killer is statistically the same. As the hydrotrope formulations all contained less Turbocharge relative to the tralkoxydim than the tank mixed formulations they were therefore as good as, or better than, the tank mixed formulations, while at the same time being less phytotoxic to crop species.

EXAMPLE 26

This example illustrates the formation of a hydrotrope formulation containing the oil-adjuvant oleyl alcohol with the hydrotrope Westvacco H240. Oleyl alcohol and Westvacco H240 were mixed together at room temperature in the ratio 1:1 by weight, leading to a mixture of water, oleyl alcohol and the potassium salt of 5(6)-carboxy-4-hexyl-2-cyclohexene-1 octanoic acid [the hydrotrope of Westvacco H240] in the ratio 30:50:20 by weight; a homogeneous single phase liquid formed spontaneously.

EXAMPLE 27

This example illustrates the formation of a hydrotrope formulation containing the oil-adjuvant Ethomeen T25 with the hydrotrope sodium salicylate. Water, Ethomeen T25 and sodium salicylate were mixed together at room temperature in the ratio 25:50:25 by weight; a homogeneous single phase liquid formed spontaneously. This hydrotrope formulation could be diluted with water, becoming less viscous but retaining its hydrotropic nature. By contrast Ethomeen T25 alone, when diluted with water formed viscous gel phases.

EXAMPLE 28

This example illustrates the formation of a hydrotrope formulation containing the oil-adjuvant Turbocharge with the hydrotrope Westvacco H240. Turbocharge and Westvacco H240 were mixed together at room temperature in the ratio 1:1 by weight, leading to a mixture of water, Turbocharge and the potassium salt of 5(6)-carboxy-4-hexyl-2-cyclohexene-1 octanoic acid [the hydrotrope of Westvacco H240] in the ratio 30:50:20 by weight; a homogeneous single phase liquid formed spontaneously. This hydrotrope formulation could be diluted with water, retaining its hydrotropic nature until at high dilution it formed a fine emulsion.

The invention claimed is:

1. An agrochemical concentrate having a continuous water-containing phase, said continuous water-containing phase comprising an oil-based adjuvant and an anionic aliphatic carboxylate hydrotrope; where the oil-based adjuvant (i) is present at a concentration of from 10 to 60% by weight of the agrochemical concentrate and (ii) is selected from fatty alcohols, fatty acids or fatty amines and simple derivatives thereof; and a ratio of the oil-based adjuvant to the hydrotrope is from 1:10 to 10:1.

2. An agrochemical concentrate as claimed in claim 1 further comprising a second phase dispersed in the continuous water-containing phase.

3. An agrochemical concentrate as claimed in claim 2 where the second phase is a solid.

4. An agrochemical concentrate as claimed in claim 2 where the second phase comprises a water-immiscible liquid.

5. An agrochemical concentrate as claimed in claim 2 where the second phase is micro-encapsulated.

6. An agrochemical concentrate as claimed in claim 2 where the second phase is a micro-emulsion.

7. An agrochemical concentrate as claimed in claim 1 further comprising an agrochemical dissolved in the continuous water-containing phase.

8. An agrochemical concentrate as claimed in claim 2 where the second phase comprises an agrochemical.

9. A continuous oil phase in which is dispersed an agrochemical concentrate as claimed in claim 1.

10. An agrochemical composition prepared by diluting an agrochemical concentrate as claimed in claim 1 in a spray-tank of water.

11. An agrochemical concentrate as claimed in claim 1, wherein the hydrotrope is a potassium salt of 5(6)-carboxy-4-hexyl-2-cyclohexene-1 octanoic acid.

12. An agrochemical concentrate as claimed in claim 11, wherein the oil-based adjuvant is oleyl alcohol.

13. An agrochemical concentrate as claimed in claim 1, wherein the continuous water-containing phase further comprises a linear or branched mineral oil.

14. An agrochemical concentrate as claimed in claim 3, further comprising a third phase comprising a water-immiscible liquid dispersed in the continuous water-containing phase.

15. An agrochemical concentrate as claimed in claim 3, wherein the second phase comprises an agrochemical.

16. An agrochemical concentrate as claimed in claim 4, wherein the second phase comprises an agrochemical.

17. An agrochemical concentrate as claimed in claim 5, wherein the second phase comprises an agrochemical.

18. An agrochemical concentrate as claimed in claim 6, wherein the second phase comprises an agrochemical.

19. An agrochemical concentrate having a continuous water-containing phase, said continuous water-containing phase comprising an oil-based adjuvant and an anionic aliphatic carboxylate hydrotrope capable of solubilising said adjuvant in said continuous water-containing phase, said concentrate further comprising (i) a second phase dispersed in the continuous water-containing phase where the second phase is a solid, and (ii) a third phase comprising a water-immiscible liquid dispersed in the continuous water-containing phase.

20. An agrochemical concentrate as claimed in claim 19 where the second phase comprises an agrochemical or the third phase comprises an agrochemical or both the second and third phases each comprise an agrochemical which may be the same or different agrochemicals.

* * * * *